US009423358B1

(12) United States Patent
Hunt et al.

(10) Patent No.: US 9,423,358 B1
(45) Date of Patent: Aug. 23, 2016

(54) WATER SIGNAL STRENGTH MAPPING TO MULTI-LAYER COATING CRACK DIMENSIONS USING TERAHERTZ (THZ) IMAGING

(71) Applicant: THE BOEING COMPANY, Chicago, IL (US)

(72) Inventors: Jeffrey H. Hunt, Chicago, IL (US); Christine A. Currie, Chicago, IL (US)

(73) Assignee: THE BOEING COMPANY, Chicago, IL (US)

( * ) Notice: Subject to any disclaimer, the term of this patent is extended or adjusted under 35 U.S.C. 154(b) by 174 days.

(21) Appl. No.: 14/172,769

(22) Filed: Feb. 4, 2014

Related U.S. Application Data

(60) Provisional application No. 61/889,962, filed on Oct. 11, 2013.

(51) Int. Cl.
*G01N 21/95* (2006.01)

(52) U.S. Cl.
CPC ...................................... *G01N 21/95* (2013.01)

(58) Field of Classification Search
CPC .............. G01N 21/88; G01N 21/8806; G01N 21/8816; G01N 21/95
See application file for complete search history.

(56) References Cited

U.S. PATENT DOCUMENTS

| | | | |
|---|---|---|---|
| 3,995,157 A | 11/1976 | Holub et al. | |
| 6,605,808 B2 | 8/2003 | Mickan et al. | |
| 6,828,558 B1 | 12/2004 | Arone et al. | |
| 7,459,687 B2 | 12/2008 | Federici et al. | |
| 7,876,423 B1 | 1/2011 | Roth | |
| 2005/0098728 A1 | 5/2005 | Alfano et al. | |
| 2007/0090294 A1 | 4/2007 | Safai et al. | |
| 2009/0121154 A1* | 5/2009 | Westphal et al. | 250/484.4 |
| 2010/0276612 A1* | 11/2010 | Norwood et al. | 250/504 R |

OTHER PUBLICATIONS

Beard, et al., "Terahertz Spectroscopy", J. Phys. Chem. B 2002, 106, 7146-7159, American Chemistry Society, published on web on Jun. 25, 2002.
Oda, et al., "Development of Terahertz Focal Plane Arrays and Handy Camera", Infrared Technology and Applications XXXVII Proc. of SPIE vol. 8012, 80121B-1 to 8012B-9, 2011.
Exter, et al., "Terahertz time-domain spectroscopy of water vapor", Optics Letters, vol. 14, No. 20, Oct. 15, 1989.
Oda, "Handy THz camera for real-time imaging", ICAS JAIMA Special Session, May 24, 2011.

* cited by examiner

*Primary Examiner* — Yara B Green
(74) *Attorney, Agent, or Firm* — Vista IP Law Group LLP; Cynthia A. Dixon

(57) ABSTRACT

A system, method, and apparatus for identifying an anomaly in a structure are disclosed. The method involves applying a quantity of a liquid onto the structure, and removing an excess of the liquid from the structure. The method further involves propagating, with at least one source, at least one transmit signal onto a location on the structure. At least one transmit signal comprises at least one terahertz frequency. Also, the method involves receiving, with at least one detector, at least one receive signal reflected from the location on the structure. Further, the method involves determining, with at least one processor, whether the location exhibits an anomaly by analyzing the intensity of at least one receive signal.

24 Claims, 6 Drawing Sheets

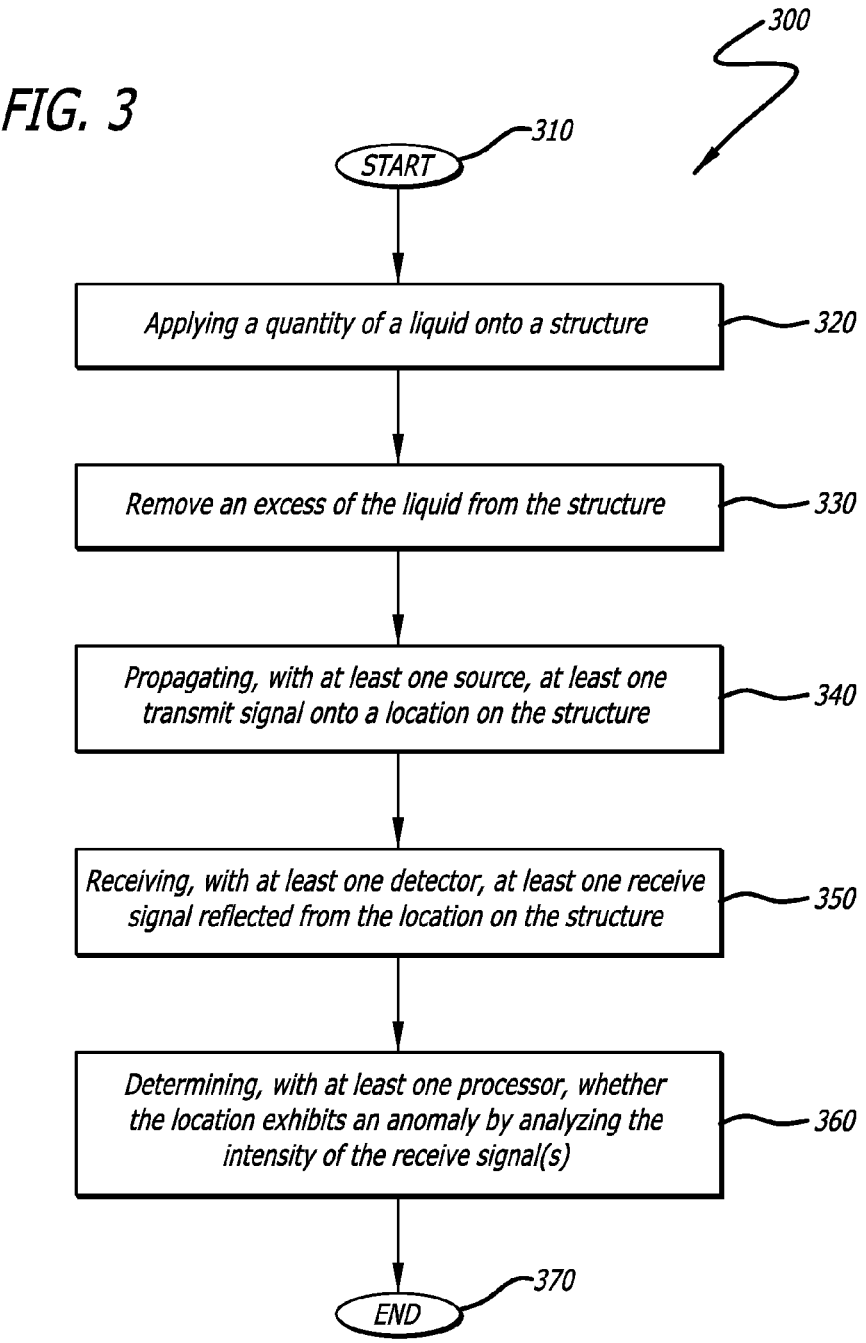

WATER SIGNAL STRENGTH MAPPING TO MULTI-LAYER COATING CRACK DIMENSIONS USING TERAHERTZ (THZ) IMAGING

CROSS-REFERENCE TO RELATED APPLICATIONS

This application claims the benefit of and priority to U.S. Provisional Application Ser. No. 61/889,962, filed Oct. 11, 2013, the contents of which are incorporated by reference herein in their entirety.

FIELD

The present disclosure relates to water signal strength mapping. In particular, it relates to water signal strength mapping to multi-layer coating crack dimensions using terahertz (THz) Imaging.

BACKGROUND

Inspection for microcracking in sealants, coatings, and composites is labor-intensive, and adequate detection is not always possible with the current inspection methods. In order for automated microcracking detection processes to offer an advantage over current methods, the precision of automated processes must be improved and ensured.

Present systems for detection of microcracking are typically contact (i.e. not remote) in nature, and are limited in speed, environment, and automation capability. Imaging systems that operate in the visible spectrum suffer from spectral interference, thereby making it difficult to discern the cracks in the material. X-ray inspection can image beneath a material surface, but the associated safety concerns with X-ray use makes their application prohibitive in a large-scale manufacturing environment. THz systems can image underneath surfaces, but poor spectral discrimination makes it difficult to obtain an adequate signal to noise ratio. A single THz imaging device can be used to generate a flat image of a surface, but this flat image does not yield information about crack depth in surface films or crack geometry in sub-surface films.

As such, there is a need for an improved microcracking detection solution.

SUMMARY

The present disclosure relates to a method, system, and apparatus for water signal strength mapping to multi-layer coating crack dimensions using terahertz (THz) Imaging. In one or more embodiments, a method for identifying an anomaly in a structure involves applying a quantity of a liquid onto the structure, and removing an excess of the liquid from the structure. The method further involves propagating, with at least one source, at least one transmit signal onto a location on the structure. In one or more embodiments, at least one transmit signal comprises at least one terahertz frequency. Also, the method involves receiving, with at least one detector, at least one receive signal reflected from the location on the structure. Further, the method involves determining, with at least one processor, whether the location exhibits the anomaly by analyzing an intensity of at least one receive signal.

In one or more embodiments, the anomaly is a defect, damage, or a foreign object. In at least one embodiment, the structure is an aircraft structure. In some embodiments, the liquid comprises water. In one or more embodiments, the removing of the excess of the liquid is achieved by using a squeegee, a cloth, a blower, a lamp, and/or heat.

In at least one embodiment, at least one source is a terahertz laser. In one or more embodiments, when at least one transmit signal comprises at least two terahertz frequencies, at least one of the frequencies is absorbed by the liquid and the liquid is transparent in at least one of the frequencies. In some embodiments, the method further involves, when at least two detectors are used to receive at least one receive signal, characterizing in three dimensions, by at least one processor, the anomaly by analyzing an intensity of at least one receive signal.

In one or more embodiments, the method further involves scanning at least one source across the structure. In some embodiments, the scanning of at least one source is performed by a robotic arm. In at least one embodiment, the method further involves, when at least one processor determines that the location exhibits an anomaly, interrupting the scanning of at least one source.

In at least one embodiment, at least one source and at least one detector are contained within one device. In some embodiments, at least one source comprises a frequency selection unit, a bandwidth control unit, a polarization selection unit, and/or an intensity selection unit. In some embodiments, at least one detector comprises a frequency selection unit, a bandwidth control unit, a polarization selection unit, and/or an intensity selection unit.

In one or more embodiments, a system for identifying an anomaly in a structure involves the structure to have a quantity of liquid applied to the structure, and to have an excess of the liquid removed from the structure. The system further involves at least one source to propagate at least one transmit signal onto a location on the structure. In one or more embodiments, at least one transmit signal comprises at least one terahertz frequency. Also, the system involves at least one detector to receive at least one receive signal reflected from the location on the structure. Further, the system involves at least one processor to determine whether the location exhibits the anomaly by analyzing an intensity of at least one receive signal.

In at least one embodiment, the excess of the liquid is removed by using a squeegee, a cloth, a blower, a lamp, and/or heat. In some embodiments, when at least one transmit signal comprises at least two terahertz frequencies, at least one of the frequencies is absorbed by the liquid and the liquid is transparent in at least one of the frequencies. In one or more embodiments, when the system involves at least two detectors to receive at least one receive signal, at least one processor characterizes in three dimensions the anomaly by analyzing the intensity of at least one receive signal.

In one or more embodiments, at least one source is further to scan across the structure. In some embodiments, the system further involves a robotic arm to scan at least one source across the structure. In at least one embodiment, when at least one processor determines that the location exhibits an anomaly, the scanning of at least one source is interrupted.

The features, functions, and advantages can be achieved independently in various embodiments of the present inventions or may be combined in yet other embodiments.

DRAWINGS

These and other features, aspects, and advantages of the present disclosure will become better understood with regard to the following description, appended claims, and accompanying drawings where:

FIG. 3 is a flow chart for the disclosed method for the operation of the system for water signal strength mapping to multi-layer coating crack dimensions using THz imaging of FIG. 1A, in accordance with at least one embodiment of the present disclosure.

DESCRIPTION

The methods and apparatus disclosed herein provide an operative system for water signal strength mapping to multi-layer coating crack dimensions using terahertz (THz) imaging. In particular, the disclosed system utilizes THz imaging technology, the resonant enhancement of water, and a correlation between the THz signal strength and crack dimensions in order to provide three-dimensional (3D) images of the microcracking and specific information about the location and orientation of the microcracking in multi-layer coating systems. Specifically, the system uses the correlation between the THz signal strength and geometry of accumulated water to measure dimensions of cracking in a multi-layer coating system with a THz imaging device. The signal received by a THz imaging device is processed so as to yield information about the volume and orientation of water applied to the surface of the multi-layer coating system. The volume and orientation of water information can then be translated into dimensions of cracking in the multi-layer coating system.

In at least one embodiment, the system employs multiple, independently controlled lenses. By superimposing data from these multiple, independently controlled lenses, the disclosed system can accelerate the inspection process for detecting microcracking in composite and/or dielectric materials, and increase the precision and accuracy of the diagnosis process.

In at least one embodiment, for the disclosed system, the frequency of the THz source is modulated as a function of the resonance frequency of the material being inspected. Because materials emit and absorb radiation at particular, unique frequencies, a more detailed characterization of the material may be obtained via differential absorption spectroscopy. The system utilizes an algorithm for particular operational frequencies based on the material to be interrogated. The off-resonant signal will be subtracted from the on-resonant signal, leaving behind only the signal that comes from the water in the crack, thereby providing a greatly enhanced signal to noise ratio.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1A:
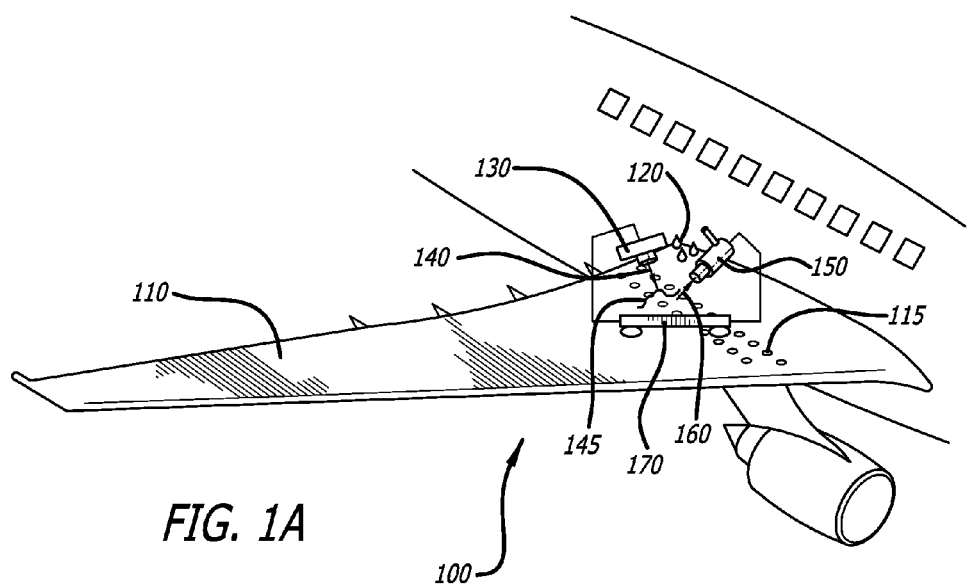
FIG. 1A is a schematic diagram of the disclosed system for water signal strength mapping to multi-layer coating crack dimensions using terahertz (THz) imaging operating on an aircraft wing, in accordance with at least one embodiment of the present disclosure.

FIG. 1A is a schematic diagram 100 of the disclosed system for water signal strength mapping to multi-layer coating crack dimensions using terahertz (THz) imaging operating on an aircraft wing 110 (including rivets 115), in accordance with at least one embodiment of the present disclosure. In this figure, a quantity of a liquid 120 (e.g., a liquid comprising water ($H_2O$)) is first applied to the aircraft wing 110 (i.e. a structure). The excess of the liquid 120 is then removed from the aircraft wing 110. The excess of the liquid 120 may be removed from the aircraft wing 110 by a squeegee, a cloth, a blower, a lamp, and/or heat. When the excess of the liquid 120 is removed from the aircraft wing 110, only liquid 120 that deposited in an anomaly (e.g., a defect, damage, foreign object, microcrack, etc.) of the aircraft wing 110 will remain on the aircraft wing 110.

After the excess of the liquid 120 is removed from the aircraft wing 110, a source 130 (e.g., a terahertz pulsed laser) propagates at least one transmit signal 140 onto a location 145 (e.g., a microcrack) on the aircraft wing 110. The transmit signal(s) 140 comprises at least one terahertz frequency. Then, a detector 150 receives at least one receive signal 160 that is reflected from the location 145 on the aircraft wing 110. At least one processor (not shown) analyzes (e.g., by using software containing an algorithm for particular operational frequencies based on the material to be interrogated) the intensity of the receive signal(s) 160 to determine whether the location 145 exhibits an anomaly (e.g., a microcrack).

In one or more embodiments, a robotic arm (not shown) is used to scan the source 130 across the aircraft wing 110 while measurements are being taken. In some embodiments, when the processor(s) determines that the location 145 exhibits an anomaly, the robotic arm interrupts (i.e. halts) the scanning of the source 130 at that particular location 145 for further investigation.

In one or more embodiments, the source 130 and the detector 150 are contained within a single device 170 (e.g. a single hardware system). For example, the source 130 and the detector 150 may be mounted on a shared platform 170. In addition, in some embodiments, the processor(s) (not shown) may also be contained within the same device 170.

Figure 1B:
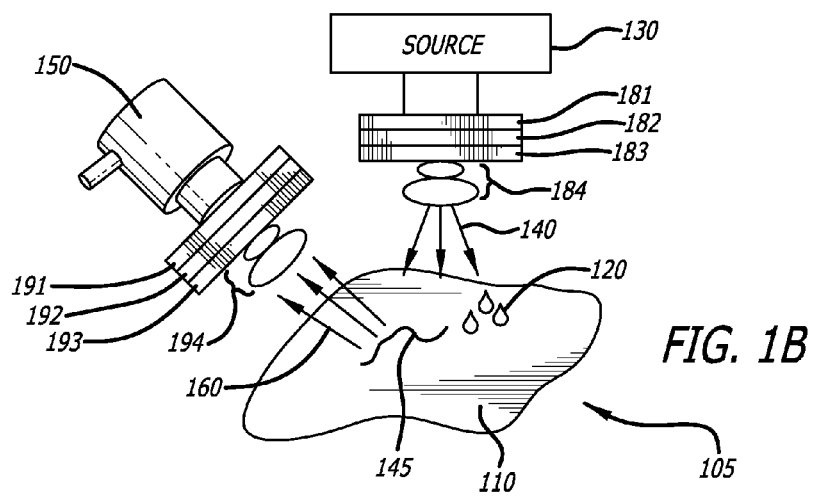
FIG. 1B is close-up view of the system for water signal strength mapping to multi-layer coating crack dimensions using THz imaging of FIG. 1A, in accordance with at least one embodiment of the present disclosure.

FIG. 1B is close-up view 105 of the system for water signal strength mapping to multi-layer coating crack dimensions using THz imaging of FIG. 1A, in accordance with at least one embodiment of the present disclosure. In this figure, it is shown that the source 130 is propagating at least one transmit signal 140 onto the location 145 (e.g., a microcrack) on the aircraft wing 110. A detector 150 then receives at least one receive signal 160 that is reflected from the location 145 on the aircraft wing 110. Then, at least one processor (not shown)

analyzes the intensity of the receive signal(s) 160 to determine whether the location 145 exhibits an anomaly (e.g., a microcrack).

In this figure, the source 130 is shown to include a frequency selection unit 181 (e.g., at least one filter), a bandwidth control unit 182 (e.g., at least one filter), a polarization control unit 183 (e.g., a polarizer), and an intensity control unit 184 (e.g., optical lenses). In addition, the detector 150 is shown to include a frequency selection unit 191 (e.g., at least one filter), a bandwidth control unit 192 (e.g., at least one filter), a polarization control unit 193 (e.g., a polarizer), and an intensity control unit 194 (e.g., optical lenses). In should be noted that in various different embodiments, more or less of these units as shown may be employed for the disclosed system.

Figure 2:
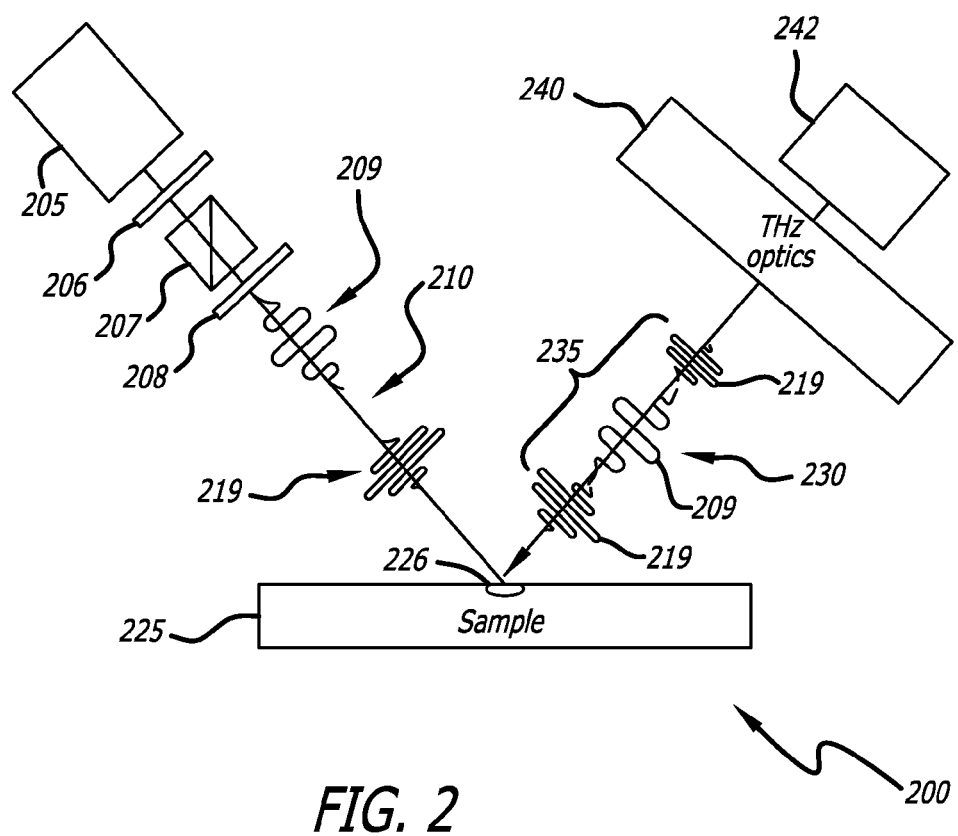
FIG. 2 is detailed schematic diagram of the system for water signal strength mapping to multi-layer coating crack dimensions using THz imaging of FIG. 1A, where the system is using two terahertz frequencies, in accordance with at least one embodiment of the present disclosure.

FIG. 2 is detailed schematic diagram 200 of the system for water signal strength mapping to multi-layer coating crack dimensions using THz imaging of FIG. 1A, where the system is using two terahertz frequencies 209, 219, in accordance with at least one embodiment of the present disclosure. In this figure, a quantity of a liquid (i.e. water, in this example) is first applied to the sample 225 (i.e. a structure). The excess of the liquid is then removed from the sample 225. When the excess of the liquid is removed from the sample 225, only liquid that deposited in an anomaly (e.g., a defect, damage, foreign object, microcrack, etc.) of the sample 225 will remain.

After the excess of the liquid is removed from the sample 225, a source 242 (e.g., a terahertz pulsed laser) emits a terahertz transmit signal 230. The transmit signal 230 comprises two different terahertz frequencies 235, where one of the frequencies 209 is absorbed by water and water is transparent in the other frequency 219.

The transmit signal 230 is first conditioned by passing through optics 240. The optics 240 may include, for example, a frequency selection unit (e.g., at least one filter), a bandwidth control unit (e.g., at least one filter), a polarization control unit (e.g., a polarizer), and/or an intensity control unit (e.g., optical lenses). The transmit signal 230 then illuminates a location 226 on the sample 225, and causes a defect at the location 226 containing residual water to emit a resonance and absorption receive signal 210. The receive signal 210 contains pulses 209 and 210 with amplitudes proportional to the amount of water absorption and water transparent frequency band energies. The amplitudes in the receive signal 210 can be used by at least one processor (not shown) to characterize the defect at the location 226 in two dimensions. The receive signal 210 emitted by the defect at the location 226 will pass through an optical intensity filter 208, a polarizer 207, and a frequency/bandwidth filter 206 before being detected by a terahertz detector 205.

FIG. 3 is a flow chart for the disclosed method 300 for the operation of the system for water signal strength mapping to multi-layer coating crack dimensions using THz imaging of FIG. 1A, in accordance with at least one embodiment of the present disclosure. At the start 310 of the method 300, a quantity of liquid (e.g., water) is applied onto a structure (e.g., an aircraft wing) 320. Then, the excess of the liquid is removed from the structure 330. At least one source then propagates at least one transmit signal (e.g., a signal comprising a least one terahertz frequency) onto a location on the structure 340. Then, at least one detector receives at least one receive signal that is reflected from the location on the structure 350. At least one processor then determines whether the location exhibits an anomaly (e.g., a microcrack) by analyzing the intensity of the receive signal(s) 360. Then, the method 300 ends 370.

Figure 4A:
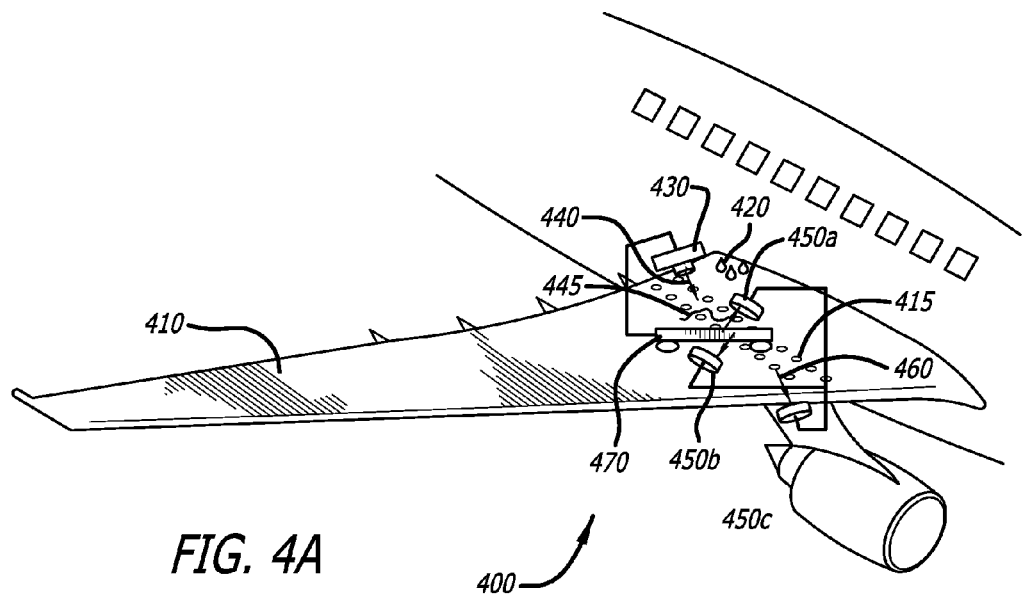
FIG. 4A is a schematic diagram of the disclosed system for water signal strength mapping to multi-layer coating crack dimensions using THz imaging operating on an aircraft wing where the system employs three detectors, in accordance with at least one embodiment of the present disclosure.

FIG. 4A is a schematic diagram 400 of the disclosed system for water signal strength mapping to multi-layer coating crack dimensions using THz imaging operating on an aircraft wing 410 (including rivets 415) where the system employs three detectors 450a, 450b, 450c, in accordance with at least one embodiment of the present disclosure. In this figure, a quantity of a liquid 420 (e.g., a liquid comprising water ($H_2O$)) is first applied to the aircraft wing 410 (i.e. a structure). The excess of the liquid 420 is then removed from the aircraft wing 410. When the excess of the liquid 420 is removed from the aircraft wing 410, only liquid 420 that deposited in an anomaly (e.g., a defect, damage, foreign object, microcrack, etc.) of the aircraft wing 410 will remain on the aircraft wing 410.

After the excess of the liquid 420 is removed from the aircraft wing 410, a source 430 (e.g., a terahertz pulsed laser) propagates at least one transmit signal 440 onto a location 445 (e.g., a microcrack) on the aircraft wing 410. The transmit signal(s) 440 comprises at least one terahertz frequency. Then, three detectors 450a, 450b, 450c each receive at least one receive signal 460 that is reflected from the location 445 on the aircraft wing 410. At least one processor (not shown) analyzes (e.g., by using software containing an algorithm for particular operational frequencies based on the material to be interrogated) the intensity of the receive signal(s) 460 received by the detectors 450a, 450b, 450c to determine whether the location 445 exhibits an anomaly (e.g., a microcrack) and, if so, to characterize the anomaly in three dimensions.

In one or more embodiments, the source 430 and the three detectors 450a, 450b, 450c are contained within a single device 470 (e.g. a single hardware system). For example, the source 430 and the detectors 450a, 450b, 450c may be mounted on a shared platform 470. In addition, in some embodiments, the processor(s) (not shown) may also be contained within the same device 470.

Figure 4B:
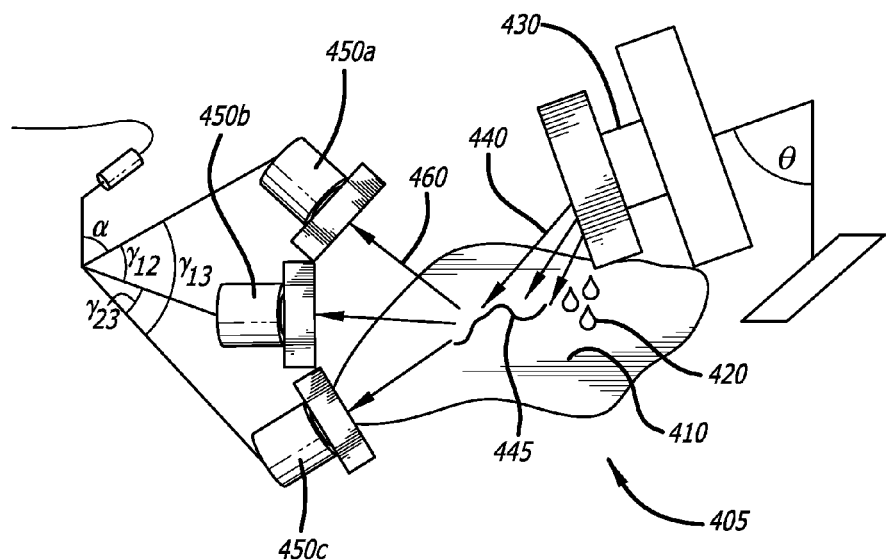
FIG. 4B is close-up view of the system for water signal strength mapping to multi-layer coating crack dimensions using THz imaging of FIG. 4A, in accordance with at least one embodiment of the present disclosure.

FIG. 4B is close-up view 405 of the system for water signal strength mapping to multi-layer coating crack dimensions using THz imaging of FIG. 4A, in accordance with at least one embodiment of the present disclosure. In this figure, it is shown that the source 430 is propagating at least one transmit signal 440 onto the location 445 (e.g., a microcrack) on the aircraft wing 410. Three detectors 450a, 450b, 450c then receive at least one receive signal 460 that is reflected from the location 445 on the aircraft wing 410. Then, at least one processor (not shown) analyzes the intensity of the receive signal(s) 460 to determine whether the location 445 exhibits an anomaly (e.g., a microcrack) and, if so, to characterize the anomaly in three dimensions.

In this figure, Angle θ is relative to the surface 410 to be inspected. While there are no hard equations regarding the angular dependence of the source 430 to the quality of the diagnostics, the source 430 should be at an angle that allows for efficient illumination without disturbance of the surface 410 or the associated detectors 450a, 450b, 450c. This implies that angles close to either normal incidence or grazing incidence should be avoided. This implies that θ values between 30 and 60 degrees are nominal choices. At the same time, other larger or smaller angles could be accommodated, and the choice of 30 to 60 should not be interpreted as precluding those other values.

For the detectors 450a, 450b, 450c, three-dimensional image reconstruction will be optimized by having the detectors 450a, 450b, 450c not placed at such severe angles relative to one another that there is no visual coordination between the detectors 450a, 450b, 450c. Therefore, $\gamma_{12}$ and $\gamma_{23}$ should be equal or within a few degrees of one another, with $\gamma_{13}$ should be between 20 and 30 degrees. It should be noted that Angle α has the same constraints as Angle θ.

Also in this figure, the source 430 may include a frequency selection unit (e.g., at least one filter), a bandwidth control unit (e.g., at least one filter), a polarization control unit (e.g., a polarizer), and an intensity control unit (e.g., optical lenses). In addition, each of the detectors 450a, 450b, 450c may also include a frequency selection unit (e.g., at least one filter), a bandwidth control unit (e.g., at least one filter), a polarization control unit (e.g., a polarizer), and an intensity control unit (e.g., optical lenses). In various different embodiments, more or less of these units as shown may be employed for the disclosed system.

Figure 5:
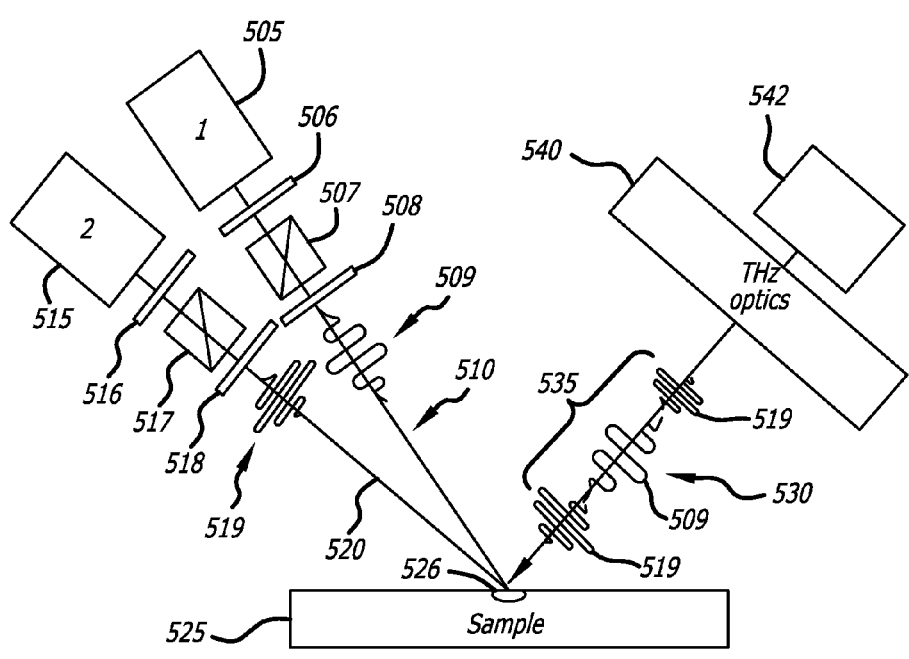
FIG. 5 is detailed schematic diagram of the system for water signal strength mapping to multi-layer coating crack dimensions using THz imaging of FIG. 4A, where the system is using two terahertz frequencies, in accordance with at least one embodiment of the present disclosure.

FIG. 5 is detailed schematic diagram 500 of the system for water signal strength mapping to multi-layer coating crack dimensions using THz imaging of FIG. 4A, where the system is using two terahertz frequencies 509, 519, in accordance with at least one embodiment of the present disclosure. In this figure, a quantity of a liquid (i.e. water, in this example) is first applied to the sample 525 (i.e. a structure). The excess of the liquid is then removed from the sample 525. When the excess of the liquid is removed from the sample 525, only liquid that deposited in an anomaly (e.g., a defect, damage, foreign object, microcrack, etc.) of the sample 525 will remain.

After the excess of the liquid is removed from the sample 525, a source 542 (e.g., a terahertz pulsed laser) emits a terahertz transmit signal 530. The transmit signal 530 comprises two different terahertz frequencies 535, where one of the frequencies 509 is absorbed by water and water is transparent in the other frequency 519.

The transmit signal 530 is first conditioned by passing through optics 540. The optics 540, for example, may include a frequency selection unit (e.g., at least one filter), a bandwidth control unit (e.g., at least one filter), a polarization control unit (e.g., a polarizer), and/or an intensity control unit (e.g., optical lenses). The transmit signal 530 then illuminates a location 526 on the sample 525, and causes a defect at the location 526 containing residual water to emit a resonance receive signal 520 and an absorption receive signal 510. The receive signal 510 contains pulse 509 with amplitudes proportional to the amount of water absorption frequency band energies, and the receive signal 520 contains pulse 519 with amplitudes proportional to the amount of water transparent frequency band energies. The amplitudes in the receive signals 510 and 520 can be used by at least one processor (not shown) to characterize the defect at the location 526 in three dimensions. The receive signal 510 emitted by the defect at the location 526 will pass through an optical intensity filter 508, a polarizer 507, and a frequency/bandwidth filter 506 before being detected by a binocular terahertz detector 205. And, the receive signal 520 emitted by the defect at the location 526 will pass through an optical intensity filter 518, a polarizer 517, and a frequency/bandwidth filter 516 before being detected by a binocular terahertz detector 215.

Figure 6:
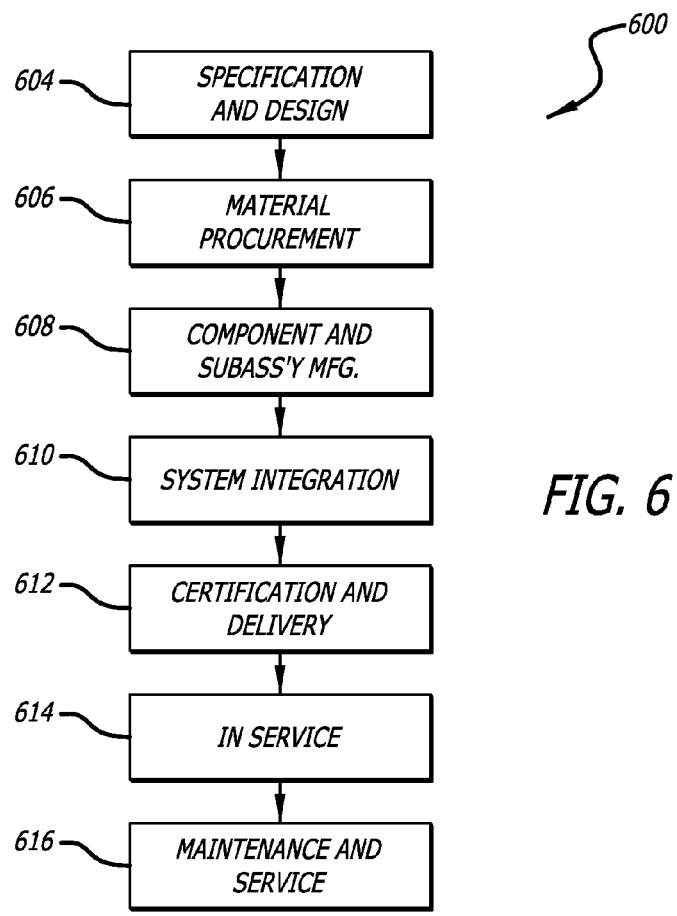
FIG. 6 is a flow diagram of aircraft production and service methodology, in accordance with at least one embodiment of the present disclosure.
Figure 7:
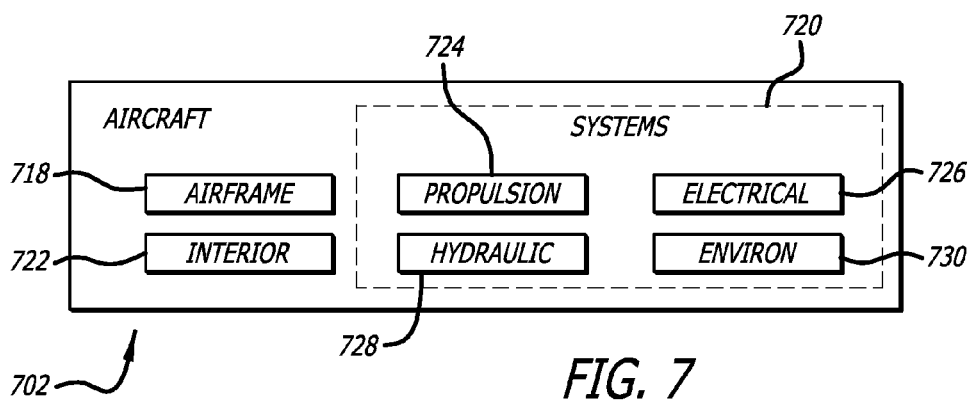
FIG. 7 is a block diagram of an aircraft, in accordance with at least one embodiment of the present disclosure.

Referring more particularly to the drawings, embodiments of the disclosure may be described in the context of an aircraft manufacturing and service method 600 as shown in FIG. 6 and an aircraft 702 (e.g., which may include aircraft wing 110 in FIG. 1A and/or aircraft wing 410 in FIG. 4A) as shown in FIG. 7. During pre-production, exemplary method 600 may include specification and design 604 of the aircraft 702 and material procurement 606. During production, component and subassembly manufacturing 608 and system integration 610 of the aircraft 702 takes place. Thereafter, the aircraft 702 may go through certification and delivery 612 in order to be placed in service 614. While in service by a customer, the aircraft 702 is scheduled for routine maintenance and service 616 (which may also include modification, reconfiguration, refurbishment, and so on).

Each of the processes of method 600 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 7, the aircraft 702 produced by exemplary method 600 may include an airframe 718 with a plurality of systems 720 and an interior 722. Examples of high-level systems 720 include one or more of a propulsion system 724, an electrical system 726, a hydraulic system 728, and an environmental system 730. Any number of other systems may be included. Although an aerospace example is shown, the principles of the invention may be applied to other industries, such as the automotive industry.

Apparatus and methods embodied herein may be employed during any one or more of the stages of the production and service method 600. For example, components or subassemblies corresponding to production process 608 may be fabricated or manufactured in a manner similar to components or subassemblies produced while the aircraft 702 is in service. Also, one or more apparatus embodiments, method embodiments, or a combination thereof may be utilized during the production stages 608 and 610, for example, by substantially expediting assembly of or reducing the cost of an aircraft 702. Similarly, one or more of apparatus embodiments, method embodiments, or a combination thereof may be utilized while the aircraft 702 is in service, for example and without limitation, to maintenance and service 616.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A method for identifying an anomaly in a structure, the method comprising:
    applying a quantity of a liquid onto the structure;
    removing an excess of the liquid from the structure;
    propagating, with at least one source, at least one transmit signal onto a location on the structure,
    wherein the at least one transmit signal comprises at least one terahertz frequency;
    receiving, with at least one detector, at least one receive signal reflected from the location on the structure;
    scanning, the at least one source, across the structure;
    determining, with at least one processor, whether the location exhibits the anomaly by analyzing an intensity of the at least one receive signal; and
    when the at least one processor determines that the location exhibits the anomaly, interrupting the scanning of the at least one source.

2. The method of claim 1, wherein the anomaly is at least one of a defect, damage, and a foreign object.

3. The method of claim 1, wherein the structure is an aircraft structure.

4. The method of claim 1, wherein the liquid comprises water.

5. The method of claim 1, wherein the removing of the excess of the liquid is achieved by using at least one of a squeegee, a cloth, a blower, a lamp, and heat.

6. The method of claim 1, wherein the at least one source is a terahertz laser.

7. The method of claim 1, wherein when the at least one transmit signal comprises at least two terahertz frequencies, at least one of the frequencies is absorbed by the liquid and the liquid is transparent in at least one of the frequencies.

8. The method of claim 1, wherein the method further comprises, when at least two detectors are used to receive the at least one receive signal, characterizing in three dimensions, by the at least one processor, the anomaly by analyzing an intensity of the at least one receive signal.

9. The method of claim 1, wherein the scanning of the at least one source is performed by a robotic arm.

10. The method of claim 1, wherein the at least one source and the at least one detector are contained within one device.

11. The method of claim 1, wherein the at least one source comprises at least one of a frequency selection unit, a bandwidth control unit, a polarization selection unit, and an intensity selection unit.

12. The method of claim 1, wherein the at least one detector comprises at least one of a frequency selection unit, a bandwidth control unit, a polarization selection unit, and an intensity selection unit.

13. A system for identifying an anomaly in a structure, the system comprising:
 the structure to have a quantity of liquid applied to the structure and to have an excess of the liquid removed from the structure;
 at least one source to propagate at least one transmit signal onto a location on the structure,
 wherein the at least one transmit signal comprises at least one terahertz frequency;
 at least one detector to receive at least one receive signal reflected from the location on the structure;
 the at least one source is further to scan across the structure;
 at least one processor to determine whether the location exhibits the anomaly by analyzing an intensity of the at least one receive signal; and
 when the at least one processor determines that the location exhibits the anomaly, the scanning of the at least one source is interrupted.

14. The system of claim 13, wherein the anomaly is at least one of a defect, damage, and a foreign object.

15. The system of claim 13, wherein the structure is an aircraft structure.

16. The system of claim 13, wherein the liquid comprises water.

17. The system of claim 13, wherein the excess of the liquid is removed by using at least one of a squeegee, a cloth, a blower, a lamp, and heat.

18. The system of claim 13, wherein the at least one source is a terahertz laser.

19. The system of claim 13, wherein when the at least one transmit signal comprises at least two terahertz frequencies, at least one of the frequencies is absorbed by the liquid and the liquid is transparent in at least one of the frequencies.

20. The system of claim 13, wherein when the system comprises at least two detectors to receive the at least one receive signal, the at least one processor characterizes in three dimensions the anomaly by analyzing an intensity of the at least one receive signal.

21. The system of claim 13, wherein the system further comprises a robotic arm to scan the at least one source across the structure.

22. The system of claim 13, wherein the at least one source and the at least one detector are contained within one device.

23. The system of claim 13, wherein the at least one source comprises at least one of a frequency selection unit, a bandwidth control unit, a polarization selection unit, and an intensity selection unit.

24. The system of claim 13, wherein the at least one detector comprises at least one of a frequency selection unit, a bandwidth control unit, a polarization selection unit, and an intensity selection unit.

* * * * *